(12) United States Patent
Baynham et al.

(10) Patent No.: US 7,288,095 B2
(45) Date of Patent: Oct. 30, 2007

(54) BONE PLATE WITH SCREW LOCK

(75) Inventors: Bret O. Baynham, Jupiter, FL (US); G. Clay Baynham, Jupiter, FL (US); Matthew G. Baynham, Jupiter, FL (US); David R. Campbell, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 577 days.

(21) Appl. No.: 10/918,518

(22) Filed: Aug. 12, 2004

(65) Prior Publication Data

US 2006/0036249 A1 Feb. 16, 2006

(51) Int. Cl.
*A61B 17/58* (2006.01)

(52) U.S. Cl. .......................................................... 606/69

(58) Field of Classification Search .................. 606/61, 606/69–71
See application file for complete search history.

(56) References Cited

U.S. PATENT DOCUMENTS

| | | | |
|---|---|---|---|
| 74,489 A | 2/1868 | Bidwel | |
| 434,503 A | 8/1890 | Corry | |
| 556,642 A | 3/1896 | Ressing | |
| 824,867 A | 7/1906 | Houghton | |
| 872,897 A | 12/1907 | Chapman et al | |
| 951,800 A | 3/1910 | Center | |
| 1,084,680 A | 1/1914 | Wegener | |
| 1,105,105 A | 7/1914 | Sherman | |
| 1,907,506 A | 5/1933 | Coburn | |
| 1,980,336 A | 11/1934 | Hoagland | |
| 2,423,511 A | 7/1947 | Luben et al. | |
| 2,757,457 A | 8/1956 | Ziegelski, Sr. | |
| 3,100,516 A | 8/1963 | Nabb | |
| 3,244,170 A | 4/1966 | McElvenny | |
| 3,386,437 A | 6/1968 | Treace | |
| 3,604,414 A | 9/1971 | Borges | |
| 3,709,219 A | 1/1973 | Halloran | |
| 3,741,205 A | 6/1973 | Markoff et al. | |
| 3,750,652 A | 8/1973 | Sherwin | |
| 3,840,014 A | 10/1974 | Ling et al. | |
| RE28,841 E | 6/1976 | Allgower et al. | |
| 3,960,147 A | 6/1976 | Murray | |
| 4,003,376 A | 1/1977 | McKay et al. | |
| 4,037,980 A | 7/1977 | Haentjens | |
| 4,069,586 A | 1/1978 | Skelton | |
| 4,102,339 A | 7/1978 | Weber et al. | |
| 4,113,227 A | 9/1978 | Cigliano | |
| 4,338,926 A | 7/1982 | Kummer et al. | |
| 4,388,921 A | 6/1983 | Sutter et al. | |
| RE31,628 E | 7/1984 | Allgower et al. | |
| 4,484,570 A | 11/1984 | Sutter et al. | |
| 4,488,543 A | 12/1984 | Tornier | |

(Continued)

*Primary Examiner*—Eduardo C. Robert
*Assistant Examiner*—Michael B Priddy
(74) *Attorney, Agent, or Firm*—McHale & Slavin, P.A.

(57) ABSTRACT

A bone plate for stabilizing adjacent vertebrae or ends of a bone has a span for extending across the discontinuity. The span has brackets for attaching to the bone. The brackets have countersunk bores terminating in apertures through which bone screws are placed in the bone. A lock screw aperture is located adjacent the countersunk bores with a portion of the sidewall forming a thin flexible tab in each bore. To prevent back-out of the bone screws, a lock screw is threaded into the lock screw aperture distorting the bore of the bone screw aperture.

10 Claims, 4 Drawing Sheets

U.S. PATENT DOCUMENTS

| | | |
|---|---|---|
| 4,493,317 A | 1/1985 | Klaue |
| 4,503,848 A | 3/1985 | Caspar et al. |
| 4,542,539 A | 9/1985 | Rowe, Jr. et al. |
| 4,651,724 A | 3/1987 | Berentey et al. |
| 4,733,657 A | 3/1988 | Kluger |
| 4,762,122 A | 8/1988 | Slocum |
| 4,794,918 A | 1/1989 | Wolter |
| 4,896,661 A | 1/1990 | Bogert et al. |
| 4,898,161 A | 2/1990 | Grundei |
| 4,943,292 A | 7/1990 | Foux |
| 4,957,495 A | 9/1990 | Kluger |
| 4,959,065 A | 9/1990 | Arnett et al. |
| 5,000,166 A | 3/1991 | Karpf |
| 5,002,544 A | 3/1991 | Klaue et al. |
| 5,019,079 A | 5/1991 | Ross |
| 5,041,113 A | 8/1991 | Biedermann et al. |
| 5,052,373 A | 10/1991 | Michelson |
| 5,053,036 A | 10/1991 | Perren et al. |
| 5,057,111 A | 10/1991 | Park |
| 5,059,194 A | 10/1991 | Michelson |
| 5,085,660 A | 2/1992 | Lin |
| 5,108,395 A | 4/1992 | Laurain |
| 5,127,912 A | 7/1992 | Ray et al. |
| 5,127,914 A | 7/1992 | Calderale et al. |
| 5,129,899 A | 7/1992 | Small et al. |
| 5,147,361 A | 9/1992 | Ojima et al. |
| 5,151,103 A | 9/1992 | Tepic et al. |
| 5,167,662 A | 12/1992 | Hayes et al. |
| 5,180,381 A | 1/1993 | Aust et al. |
| 5,190,544 A | 3/1993 | Chapman et al. |
| 5,209,751 A | 5/1993 | Farris et al. |
| 5,217,497 A | 6/1993 | Mehdian |
| 5,234,430 A | 8/1993 | Huebner |
| 5,300,073 A | 4/1994 | Ray et al. |
| 5,338,197 A | 8/1994 | Kwan |
| 5,364,399 A | 11/1994 | Lowery et al. |
| 5,380,328 A | 1/1995 | Morgan |
| 5,397,363 A | 3/1995 | Gelbard |
| 5,423,826 A | 6/1995 | Coates et al. |
| 5,456,685 A | 10/1995 | Huebner |
| 5,478,340 A | 12/1995 | Kluger |
| 5,478,348 A | 12/1995 | Bajada |
| 5,492,442 A | 2/1996 | Lasner |
| 5,520,690 A | 5/1996 | Errico et al. |
| 5,527,314 A | 6/1996 | Brumfield et al. |
| 5,531,554 A | 7/1996 | Jeanson et al. |
| 5,531,746 A | 7/1996 | Errico et al. |
| 5,545,163 A | 8/1996 | Miller et al. |
| 5,545,165 A | 8/1996 | Biedermann et al. |
| 5,549,612 A | 8/1996 | Yapp et al. |
| 5,558,674 A | 9/1996 | Heggeness et al. |
| 5,562,663 A | 10/1996 | Wisnewski et al. |
| 5,562,672 A | 10/1996 | Huebner et al. |
| 5,578,034 A | 11/1996 | Estes |
| 5,601,553 A | 2/1997 | Trebing et al. |
| 5,603,713 A | 2/1997 | Aust et al. |
| 5,607,426 A | 3/1997 | Ralph et al. |
| 5,616,142 A | 4/1997 | Yuan et al. |
| 5,616,144 A | 4/1997 | Yapp et al. |
| 5,643,265 A | 7/1997 | Errico et al. |
| 5,662,652 A | 9/1997 | Schafer et al. |
| 5,672,175 A | 9/1997 | Martin |
| 5,676,666 A | 10/1997 | Oxland et al. |
| 5,676,703 A | 10/1997 | Gelbard |
| 5,735,853 A | 4/1998 | Olerud |
| 5,735,899 A | 4/1998 | Schwartz et al. |
| 5,755,796 A | 5/1998 | Ibo et al. |
| 5,766,254 A | 6/1998 | Gelbard |
| D402,032 S | 12/1998 | Stone |
| 5,849,012 A | 12/1998 | Abboudi |
| D406,646 S | 3/1999 | Stone |
| 5,876,402 A | 3/1999 | Errico et al. |
| 5,876,446 A | 3/1999 | Agrawal et al. |
| 5,954,722 A | 9/1999 | Bono |
| 6,022,350 A | 2/2000 | Ganem |
| 6,030,389 A | 2/2000 | Wagner et al. |
| 6,152,927 A | 11/2000 | Farris et al. |
| 6,224,602 B1 | 5/2001 | Hayes |
| 6,231,610 B1 | 5/2001 | Geisler |
| 6,342,055 B1 | 1/2002 | Eisermann et al. |
| 6,398,783 B1 | 6/2002 | Michelson |
| 6,436,142 B1 | 8/2002 | Paes et al. |
| 6,454,771 B1 | 9/2002 | Michelson |
| 6,669,700 B1 | 12/2003 | Farris et al. |
| 6,730,127 B2 | 5/2004 | Michelson |
| 6,740,088 B1 | 5/2004 | Kozak et al. |
| 6,936,051 B2 | 8/2005 | Michelson |
| 2004/0102773 A1 | 5/2004 | Morrison et al. |

BONE PLATE WITH SCREW LOCK

FIELD OF THE INVENTION

This invention relates to the field of orthopedic surgery and to bone plates which are affixed to bone by screws.

BACKGROUND OF THE INVENTION

The use of bone pins and plates for reducing fractures is well known in orthopedic medicine. The pins and plates extend across discontinuities in a bone to fix the broken ends in relation to each other to reduce pain and promote rapid healing without deformity. These devices are secured to the bone by bone screws or nails driven into the bone. More recently, pins, rods, plates and cages have been used to stabilize bone and joints that have deteriorated naturally or as a result of prior trauma.

The interface between the bone screws and the bone presents problems of stability and long term usage that have been addressed in different ways. One of the major problems is usually termed as back-out. This defines the condition in which the screws attaching the plate to the bone loosen over time, either relative to the bone or the plate or both. Severe back-out results in the bone screw working itself out of the bone and/or plate resulting in instability of the bone or joint. This situation results in increasing pain and danger from the instability, as well as, the movement of the screw. There may be several reasons for the back-out but anatomical stresses from body movements contributes greatly to the problem.

Bone plates are usually attached to adjacent vertebrae to reduce pain due to injury or deterioration of the intermediate disk. The plate spans the intervertebral space to stabilize the vertebrae. Also, bone plates are used to reduce breaks and stabilize bones in other parts of the body. Pedicle screws or bone screws are inserted through apertures in the opposite ends of the plate into the respective vertebrae or on opposite sides of a break. Due to anatomical forces on the skeleton, the screws sometimes back out of the bones and plates.

Prior art devices address the problem of back-out by use of secondary locking screws that hold the bone screws in the plate. The locking device engages the head of the bone screw and is tightened to fix the screw to the plate and, thus, the bone. Such devices are not particularly suited for deployment on the anterior aspect of the spine because of the close proximity of vital soft tissue organs which dictate a smooth, low profile, contoured surface. Michelson, U.S. Pat. No. 6,454,771, discloses a bone plate for anterior cervical fixation. The plate has several holes for receiving bone screws. A locking screw mechanism is used to overlay the screw heads.

An expandable insert for placement between vertebrae is disclosed by Paes et al, U.S. Pat. No. 6,436,142. The device is in the nature of a lag screw and can expand with the insertion of an expansion screw.

U.S. Pat. No. 6,342,055 to Eisermann et al discloses a bone plate with bone screws having a snap-in retainer securing the heads to the plate.

Geisler, U.S. Pat. No. 6,231,610, discloses a bone plate with diverging bone screws and serrations on the plate to increase holding power.

U.S. Pat. No. 6,224,602 to Hayes discloses a bone plate with multiple bone screw holes which may be covered by a sliding locking plate. The bone plate has an undercut channel to hold the locking plate in contact with the screw heads. The locking plate is held to the plate by a locking screw once it is slid to the desired position.

Aust et al, U.S. Pat. No. 5,603,713, discloses an anterior lumbar plate attached by screws with various angular connections to the spine.

Published application, US 2004/0102773 A1, to Morrison et al, uses the ends of the bone plate to cover the heads of the bone screws.

U.S. Pat. No. 6,740,088 B1, to Kozak et al uses extra set screws to interfere with the heads of the bone screws.

U.S. Pat. No. 6,730,127 B2 to Michelson attaches an overlay to the plate to partially cover the heads of the screws.

What is needed in the art is a bone plate with a simple screw lock that does not add extraneous components to the combination.

SUMMARY OF THE PRESENT INVENTION

Disclosed is a bone plate for stabilizing adjacent vertebrae. The bone plate is based on an elongated span having a first end and a second end with a first bracket on the first end adapted to engage a first vertebrae and a second bracket on the second end adapted to engage a second vertebrae. The first bracket includes a first bone screw aperture and a second bone screw aperture with a lock screw aperture located therebetween, each bone screw aperture having s countersunk bore. A lock screw aperture includes an internally threaded sidewall with a portion of the sidewall formed from a thin flexible tab in the countersunk bore and a second portion of the sidewall forming a thin flexible tab in the second countersunk bore. The first and second tabs are adapted to distort the countersunk bores.

The bone plate may include an intermediate bracket on the span between the first and second bracket with a bone screw aperture in the intermediate bracket having a countersunk bore. A lock screw aperture is placed adjacent to the bone screw aperture having the sidewall that distorts the bore for locking of the screw.

Therefore, it is an objective of this invention to provide a bone plate with an integral one-piece screw lock.

It is another objective of this invention to provide a low profile bone plate with countersunk bone screw apertures therethrough.

It is a further objective of this invention to provide a bone plate to span a plurality of discontinuaties in the bone.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
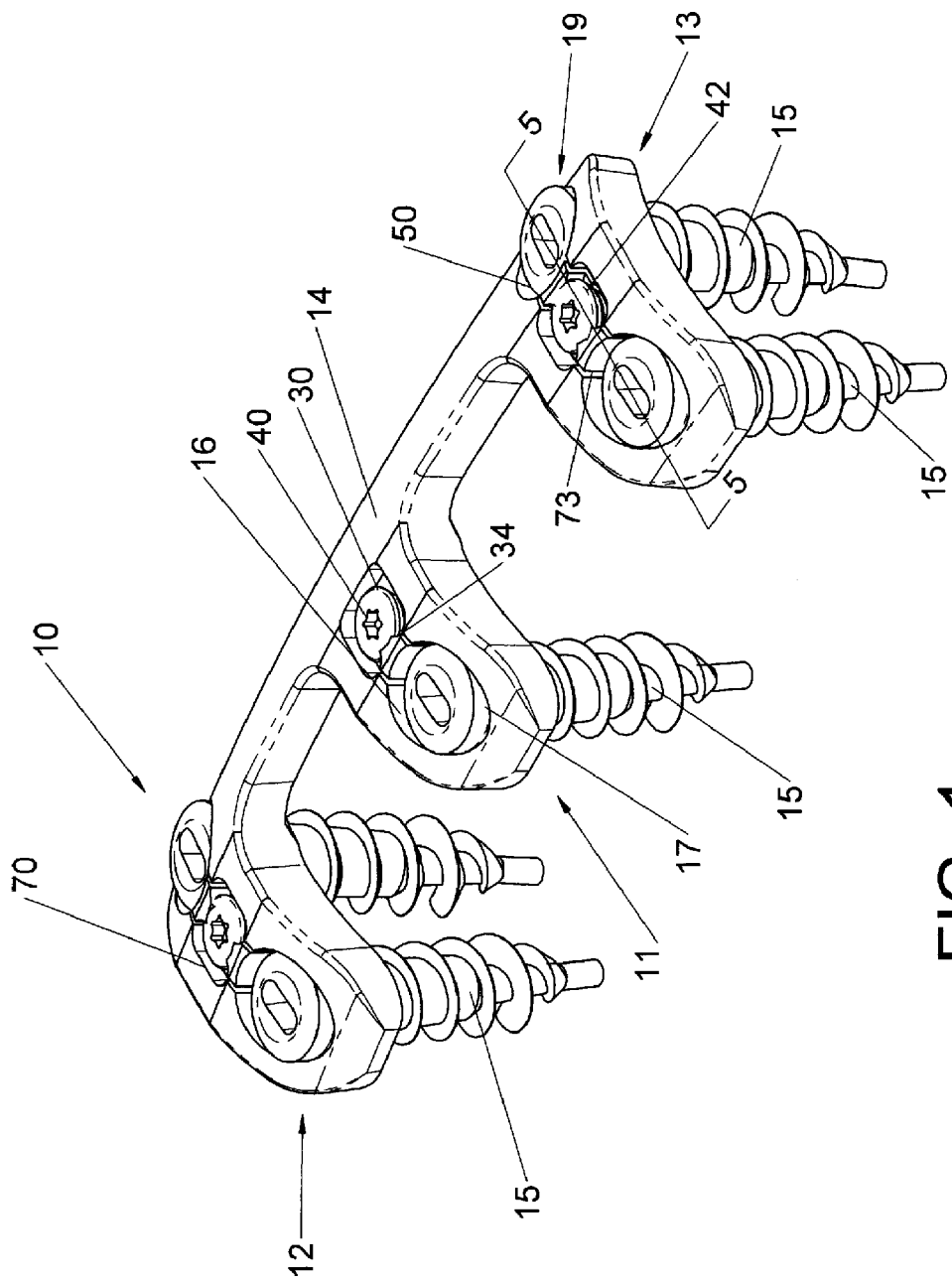
FIG. 1 is a perspective of the assembled bone plate and screws of this invention.

In FIG. 1, the one piece bone plate or implant 10 is shown with an intermediate anchoring bracket 11 and end anchoring brackets 12, 13. As shown, the intermediate bracket has a single aperture accepting a bone or pedicle screw 15. This construction results in a stronger span 14. However, this bracket could be made the same as the end brackets. The bracket 11 has a semi-spherical countersunk bore terminating with an aperture 16 with an enlarged opening 17 on the distal side of the plate and a smaller opening 18 proximal to the bone.

Adjacent to the countersunk aperture 16 is a smaller lock screw aperture 30 with internal threads 31. A thin wall 32 separates the countersunk bore and the lock screw aperture. This thin wall 32 has two vertical slits 33, 34 extending from the distal side of the plate toward the proximal side. The slits 33, 34 terminate short of the proximal surface of the plate 10 resulting in a flexible tab 35. The tab 35 has a portion of the threads 31 on one side.

Figure 3:
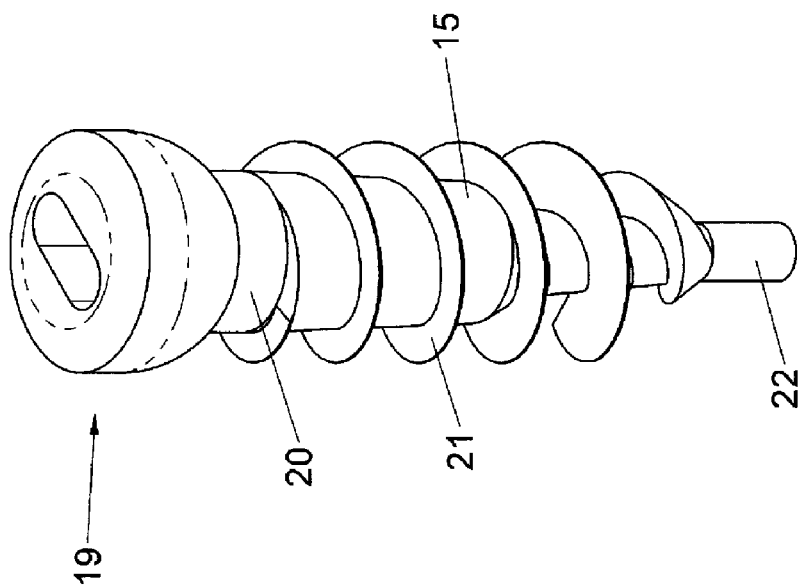
FIG. 3 is a perspective of a bone screw of this invention.

The head 19 of the bone screw 15 has a spherical shape, as illustrated in FIG. 3, with an enlarged head and a smaller diameter portion connected to the shaft 20. A helical thread 21 is formed on the shaft and shaped to gain maximum purchase within the bone. The leading end of the screw has a guide point 22 to follow pilot holes in the bone. As the bone screw 15 is driven into the bone, the head 19 of the screw seats in the spherical countersunk bore drawing the plate tightly against the bone.

Figure 2:
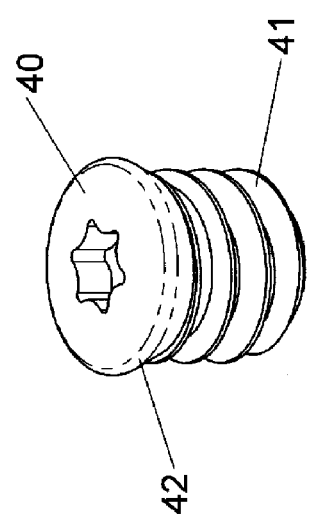
FIG. 2 is a perspective of the lock screw of this invention.

When the bone screw 15 has been fully tightened, a lock screw 40, shown in FIG. 2, is threaded into the lock screw aperture 30 with the external threads 41 engaging the internal threads 31. The diameter of the lock screw 40 is slightly larger than the diameter of the lock screw aperture. The tightening of the lock screw in the aperture displaces the tab 35 to distort the spherical countersunk bore and bind the head of the bone screw against the tab forming a friction lock. In the alternate, the head 42 of the lock screw is of greater diameter than the lock screw aperture such that the head acts as a wedge to force the tab 35 against the head of the bone screw. Further, the inter-engaged threads 31 and 41 are displaced jamming the threads to prevent backing out.

Figure 4:
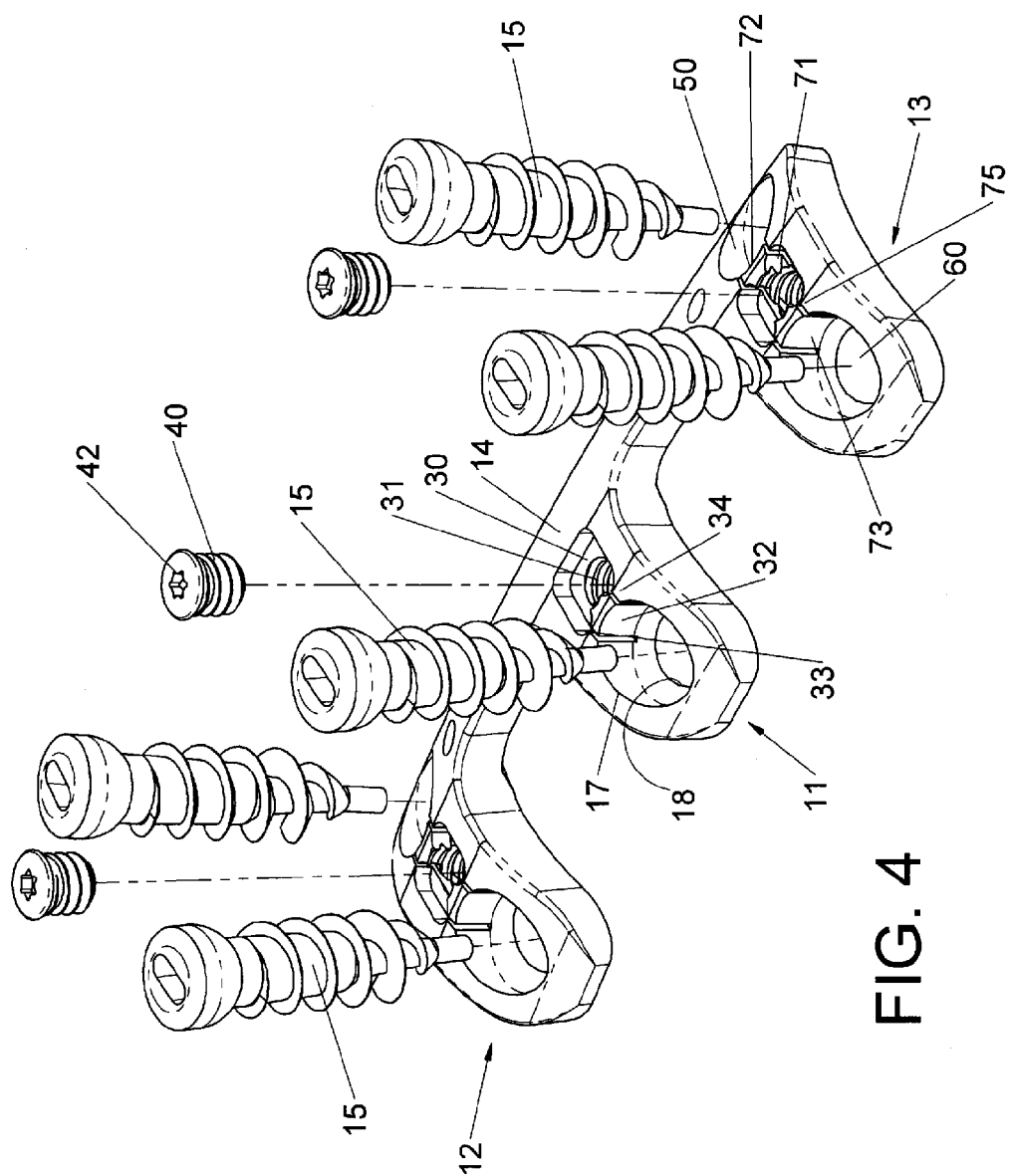
FIG. 4 is a perspective of the bone plate of this invention.
Figure 5:
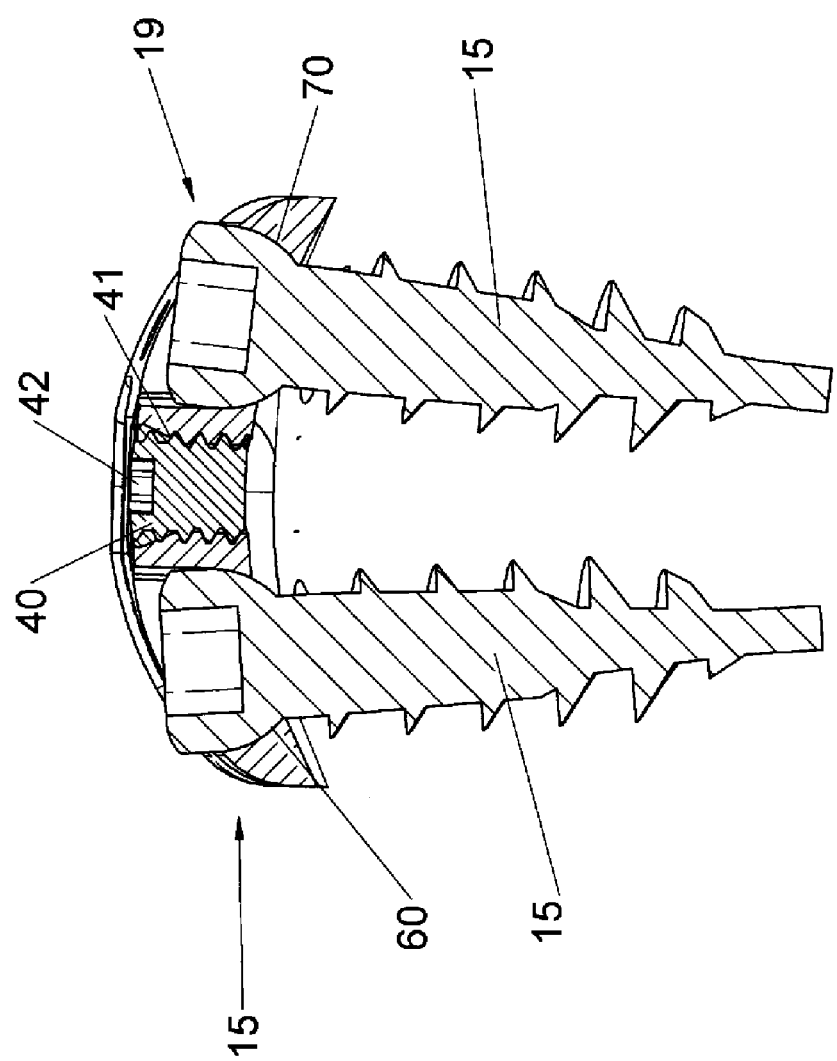
FIG. 5 is a cross section the bone plate along line 5-5 of FIG. 1.

As shown in FIGS. 1, 4 and 5, the end brackets 12, 13 have two countersunk apertures accepting bone screws. A lock screw aperture is located between the countersunk apertures. The lock screw aperture shares a portion of its sidewall with each of the bone screw bores. Both end brackets are identical therefore, for brevity, only one bracket will be described in detail. The same reference numerals will be used for the same components of each end bracket.

The end brackets have two semi-spherical countersunk apertures 50, 60 with an adjacent lock screw aperture 70 located between them. Portions of the sidewall 71 of the lock screw aperture form thin flexible tab 72 in aperture bore 50 and flexible tab 73 in aperture bore 60. The tabs are formed by vertical slits in the sidewall 71. As shown in FIG. 4, flexible tab 73 has margins formed by slits 74 and 75. These tabs function in the same manner as the tab 35 in the intermediate bracket. However, both tabs 72, 73 are operated by only one lock screw 40. When the lock screw is threaded into the lock screw aperture, the bone screws are wedged in the countersunk bores.

As shown in FIG. 5, the bone plate is arcuately shaped to conform closely with the bone on the proximal side. The distal side is also arcuately shaped to follow the contour of the bone to reduce trauma or irritation of adjacent soft tissue.

The bone plate and screws may be fabricated from surgical steel, other suitable alloys, ceramics, and polymers or combinations thereof with the requisite strength and nontoxicity in the body.

The bone plates and screws may be supplied in kit form with different sized screws for selection due to anatomical necessities.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

What is claimed is:

1. A bone plate for attachment to bone across discontinuaties comprising an elongated span having a first end and a second end, a first bracket on said first end and a second bracket on said second end, said first bracket and said second bracket each having a lock screw aperture and a bone screw aperture adjacent to each other, said lock screw aperture having a sidewall with internal threads, a portion of said sidewall forming a thin flexible tab separating said bone screw aperture and said lock screw aperture, a lock screw having external threads adapted to engage said internal threads in said sidewall and distort said bone screw aperture and said internal threads.

2. A bone plate of claim 1 comprising a counter sunk bore surrounding said bone screw aperture, said counter sunk bore having a sidewall, said tab including a portion of said counter sunk bore sidewall.

3. A bone plate of claim 1 comprising an intermediate bracket on said span between said first end and said second end, a lock screw aperture in said intermediate bracket, a bone screw aperture in said intermediate bracket adjacent said lock screw aperture, a common wall separating said lock screw aperture and said bone screw aperture, a pair of spaced apart slits in said common wall, said common wall between said slits forming a flexible tab, internal threads in said lock screw aperture on said tab, a bone screw adapted to be inserted into said bone screw aperture, a lock screw adapted to be inserted in said lock screw aperture, said tab adapted to distort said lock screw aperture.

4. A bone plate of claim 3 comprising a counter sunk bore surrounding said bone screw aperture in said intermediate bracket, said counter sunk bore having a sidewall, said tab including a portion of said counter sunk bore sidewall.

5. A bone plate of claim 1 comprising said first bracket and said second bracket each having a second bone screw aperture, said lock screw aperture located between each said bone screw aperture and each said second bone screw aperture, a second portion of said sidewall forming a second thin flexible tab separating said second bone screw aperture and said lock screw aperture.

6. A bone plate of claim 5 comprising an intermediate bracket on said span between said first end and said second end, a lock screw aperture in said intermediate bracket, a bone screw aperture in said intermediate bracket adjacent said lock screw aperture, a common wall separating said lock screw aperture and said bone screw aperture, a pair of spaced apart slits in said common wall, said common wall between said slits forming a flexible tab, internal threads in said lock screw aperture on said tab, a bone screw adapted to be inserted into said bone screw aperture, a lock screw adapted to be inserted in said lock screw aperture, said tab adapted to distort said lock screw aperture.

7. A bone plate of claim 5 comprising a counter sunk bore surrounding said bone screw aperture and said second bone screw aperture, each said bore having a sidewall, said tab and said second tab each including a portion of said bore sidewall.

8. A bone plate of claim 6 comprising a counter sunk bore surrounding said bone screw aperture in said intermediate bracket, said counter sunk bore having a sidewall, said tab including a portion of said counter sunk bore sidewall.

9. A bone plate for stabilizing adjacent vertebrae comprising an elongated span having a first end and a second end, a first bracket on said first end adapted to engage a first vertebrae, a second bracket on said second end adapted to engage a second vertebrae, said first bracket including a first bone screw aperture and a second bone screw aperture with a lock screw aperture located between said first and said second bone screw apertures, said first and second bone screw apertures surrounded by countersunk bores, said lock screw aperture having an internally threaded sidewall, a first portion of said sidewall forming a first thin flexible tab in said first countersunk bore and a second portion of said sidewall forming a second thin flexible tab in said second countersunk bore, said first and second tabs adapted to distort said countersunk bores.

10. A bone plate of claim 9 comprising an intermediate bracket on said span between said first and second brackets, a bone screw aperture in said intermediate bracket having a countersunk bore, a lock screw aperture adjacent said bone screw aperture, said lock screw aperture having a sidewall, a portion of said sidewall forming a thin flexible tab in said countersunk bore, said tab adapted to distort said counter sunk bore.

* * * * *